United States Patent
Chen

(10) Patent No.: US 10,251,993 B2
(45) Date of Patent: Apr. 9, 2019

(54) HEMODIALYSIS DEVICE

(71) Applicant: Feng Chen, Nanning (CN)

(72) Inventor: Feng Chen, Nanning (CN)

( * ) Notice: Subject to any disclaimer, the term of this patent is extended or adjusted under 35 U.S.C. 154(b) by 284 days.

(21) Appl. No.: 15/242,427

(22) Filed: Aug. 19, 2016

(65) Prior Publication Data

US 2017/0246370 A1 Aug. 31, 2017

(30) Foreign Application Priority Data

Feb. 26, 2016 (CN) .......................... 2016 1 0106083
Feb. 26, 2016 (CN) ...................... 2016 2 0144515 U

(51) Int. Cl.
| | | |
|---|---|---|
| *A61M 1/36* | (2006.01) | |
| *A61M 1/16* | (2006.01) | |
| *A61M 25/00* | (2006.01) | |
| *A61M 1/28* | (2006.01) | |
| *A61M 39/10* | (2006.01) | |
| *A61M 25/06* | (2006.01) | |

(52) U.S. Cl.
CPC ........ *A61M 1/3661* (2014.02); *A61M 1/1601* (2014.02); *A61M 1/1664* (2014.02); *A61M 1/285* (2013.01); *A61M 25/003* (2013.01); *A61M 2025/0031* (2013.01); *A61M 2025/0034* (2013.01); *A61M 2025/0039* (2013.01); *A61M 2025/0681* (2013.01); *A61M 2039/1027* (2013.01); *A61M 2039/1033* (2013.01); *A61M 2039/1088* (2013.01); *A61M 2205/3337* (2013.01)

(58) Field of Classification Search
CPC .. A61M 2025/0031; A61M 2025/0034; A61M 2025/0039; A61M 2025/0681; A61M 1/1601; A61M 1/1664; A61M 1/285; A61M 1/3661; A61M 2039/1027; A61M 2039/1033; A61M 2039/1088; A61M 2205/3337; A61M 25/003

See application file for complete search history.

(56) References Cited

U.S. PATENT DOCUMENTS

| | | | |
|---|---|---|---|
| 4,218,321 A | 8/1980 | Sasaki et al. | |
| 4,235,231 A | 11/1980 | Schindler et al. | |
| 4,777,953 A | 10/1988 | Ash et al. | |
| 5,350,358 A * | 9/1994 | Martin .............. | A61M 25/0041 604/43 |
| 6,030,358 A | 2/2000 | Odland | |
| 6,561,996 B1 | 5/2003 | Gorsuch | |

(Continued)

*Primary Examiner* — John Kim
(74) *Attorney, Agent, or Firm* — Carr & Ferrell LLP

(57) ABSTRACT

A hemodialysis device is described herein. An exemplary hemodialysis device includes an import tube, a dialysis tube, and an export tube. The dialysis tube includes an inner dialysis tube, a dialysis membrane and an outer dialysis tube. The inner dialysis tube is within the dialysis membrane, which is within the outer dialysis tube. An inlet and an outlet of the inner tube are disposed at a first end of the outer dialysis tube. The inlet of the inner dialysis tube is coupled to the import tube and the outlet of the inner dialysis tube is coupled to the export tube. The dialysis tube is inserted into an artery of a patient, and thereby performs hemodialysis within the body. Since the hemodialysis in performed within the artery instead of drawing blood out of the body, the hemodialysis device will minimally affect blood pressure, which is more economic and safe.

7 Claims, 3 Drawing Sheets

(56) References Cited

U.S. PATENT DOCUMENTS

| | | |
|---|---|---|
| 6,849,183 B2 | 2/2005 | Gorsuch et al. |
| 7,828,763 B2 | 11/2010 | Wright et al. |
| 2004/0009096 A1 | 1/2004 | Wellman |
| 2005/0036983 A1 | 2/2005 | Simon et al. |

* cited by examiner

HEMODIALYSIS DEVICE

CROSS-REFERENCE TO RELATED APPLICATIONS

This non-provisional patent application claims the priority benefit of Chinese Patent Application Number 201610106083.1 filed on Feb. 26, 2016, and claims the priority benefit of Chinese Patent Application Number 201620144515.3 filed on Feb. 26, 2016, which are hereby incorporated by reference herein in their entirety.

FIELD OF THE INVENTION

The present disclosure relates generally to medical equipment and, more particularly, to hemodialysis devices.

BACKGROUND OF THE INVENTION

Currently, there exist two main therapies to relieve edema: medicinal diuretics and hemodialysis. A method utilizing medicinal diuretics uses medicine to increase the volume of patients' urine, thereby drawing out the excess water in the body. Hemodialysis involves withdrawing patients' blood, and filtering the blood with an in vitro instrument to remove excess water. Then, the concentrated blood is transferred back into the body to relieve the edema.

Hemodialysis is also a regular treatment of acute or chronic renal dysfunction, acute drug poisoning, and pesticide poisoning. Tens of millions of patients with chronic renal failure use hemodialysis as regular treatment to sustain life, and the population of patients increases year by year. Dialysis involves a dialysate solution on both sides of a semipermeable membrane flowing from a first, high concentration side to a second, low concentration side by way of diffusion, osmosis and ultrafiltration until reaching dynamic equilibrium. By dispersion and ultrafiltration between blood and a dialysate solution, hemodialysis is achieved.

Each therapy currently has significant disadvantages. Medicinal diuretics may require a large number of medicines, which may cause side effects and drug resistance. Moreover, critically ill patients may suffer with kidney failure, thus blocking the diuresis. Furthermore, hemodialysis typically requires withdrawing blood from the body, which may change a patient's blood volume sharply and cause instabilities in blood pressure and even death. Hemodialysis can only last for several hours, so it cannot provide sustained, long-term and steady dialysis for patients. In addition, the dialysis equipment is too large to transfer easily, thus the patient will always need to be transferred to a dialysis room or the dialysis machine will need to be transferred to the patients' bedside—increasing the difficulty of the treatment. Moreover, the equipment is expensive and may cost millions of dollars. Unfortunately, these deficiencies have never been addressed previously.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

Some embodiments of the present disclosure include a hemodialysis device which may include: an import tube having an inlet and an outlet; an export tube having an inlet and an outlet; a dialysis tube having: an outer dialysis tube having a first end, a second end, and an intermediate cavity; an inner dialysis tube disposed within the intermediate cavity, the inner dialysis tube having an inlet, an outlet, and an interior cavity, the inlet and the outlet disposed at the first end of the outer dialysis tube; and a dialysis membrane, the interior cavity being in partial fluid communication with the intermediate cavity across the dialysis membrane; and a lock coupling the outlet of the import tube to the inlet of the inner dialysis tube, and coupling the inlet of the export tube to the outlet of the inner dialysis tube.

Various embodiments of the present disclosure include a dialysis tube for a hemodialysis device which may include: an outer dialysis tube having a first end, a second end, and an intermediate cavity; an inner dialysis tube disposed within the intermediate cavity, the inner dialysis tube having an inlet, an outlet, and an interior cavity, the inlet and the outlet disposed at the first end of the outer dialysis tube; and a dialysis membrane, the interior cavity being in partial fluid communication with the intermediate cavity across the dialysis membrane.

In some embodiments, the present disclosure includes a method for performing hemodialysis within an artery, the method including: inserting a dialysis tube into the artery, the dialysis tube having an outer dialysis tube, an inner dialysis tube, and a dialysis membrane, the inner dialysis tube disposed within an intermediate cavity of the outer dialysis tube, wherein the inner dialysis tube has an inlet coupled to an import tube, an outlet coupled to an export tube, and an interior cavity, the inlet and the outlet disposed at a first end of the outer dialysis tube; driving dialysate solution through the import tube into the interior cavity of the inner dialysis tube; extracting excess fluid from blood flowing within the artery, the excess fluid flowing from the blood in the intermediate cavity, across the dialysis membrane, and into the dialysate solution in the interior cavity; and withdrawing the excess fluid and the dialysate solution from the inner dialysis tube to the export tube

BRIEF DESCRIPTION OF DRAWINGS

The accompanying drawings, where like reference numerals refer to identical or functionally similar elements throughout the separate views, together with the detailed description below, are incorporated in and form part of the specification, and server to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
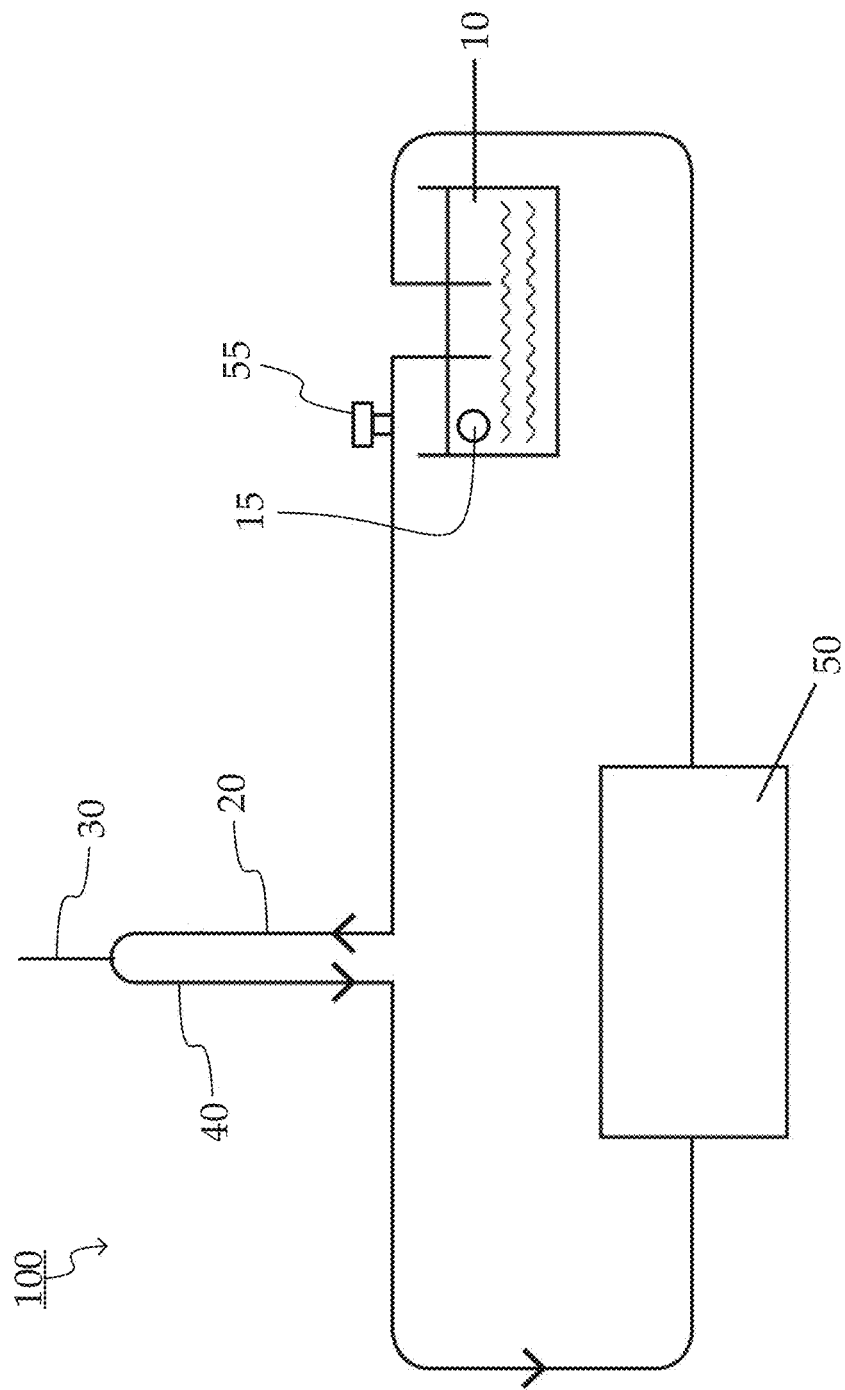
FIG. 1 is a diagrammatic representation of an exemplary hemodialysis device according to the present disclosure.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated. The terminology used herein is for the purpose of describing particular embodiments only and is not intended to be limiting of the technology. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

The present disclosure is directed to various embodiments of a hemodialysis device. The hemodialysis device comprises a dialysis tube that is placed within an artery of the human body. Diffusion, osmosis and ultrafiltration occurs at the dialysis tube within the artery, thus blood does not have to be withdrawn from the patient. Advantageously, the hemodialysis occurs within the artery and will have no effect or a minimum effect on the patient's blood pressure, which is more economic and safe.

FIG. 1 illustrates an exemplary hemodialysis device 100 having a dialysate tank 10, a temperature control device 15, an import tube 20 of the dialysate, a dialysis tube 30, an export tube 40 of the dialysate, a peristaltic pump 50, and a speed regulating valve 55. FIG. 1 depicts a flow diagram of dialysate solution through the hemodialysis device 100, from the dialysate tank 10, to the import tube 20, to the dialysis tube 30, to the export tube 40, through the peristaltic pump 50, and returning to the dialysate tank 10. The dialysate tank 10 is coupled to an inlet of the import tube 20. An outlet of the import tube 20 and an inlet of the export tube 40 are coupled to the dialysis tube 30. An outlet of the export tube 40 is coupled to the peristaltic pump 50, which is then coupled with the dialysate tank 10 with a tube. It is to be understood that pump 50 may include a peristaltic pump or other suitable pump to drive the dialysate solution through the hemodialysis device 100.

In some embodiments, the speed regulating value 55 is disposed between the dialysate tank 10 and the import tube 20. A flow rate of the dialysate solution entering the import tube 20 is controlled by the speed regulating valve 55. Thus, the flow rate may be adjusted automatically or manually by a physician or user to relieve patient discomfort and ensure efficiency of dialysis. It is to be understood that the speed regulating valve 55 may be disposed at various positions along the path of the dialysate solution to control the flow rate.

In one or more embodiments, the temperature control device 15 regulates a temperature of the dialysate solution. The temperature of the dialysate solution may be set to any suitable temperature, or specifically to the normal temperature of the blood that the patient needs. It is to be understood that temperature control device 15 may be disposed within the dialysate tank 10, or at any position along the path of the dialysate solution to control the temperature of dialysate solution entering the dialysis tube 30.

Figure 2:
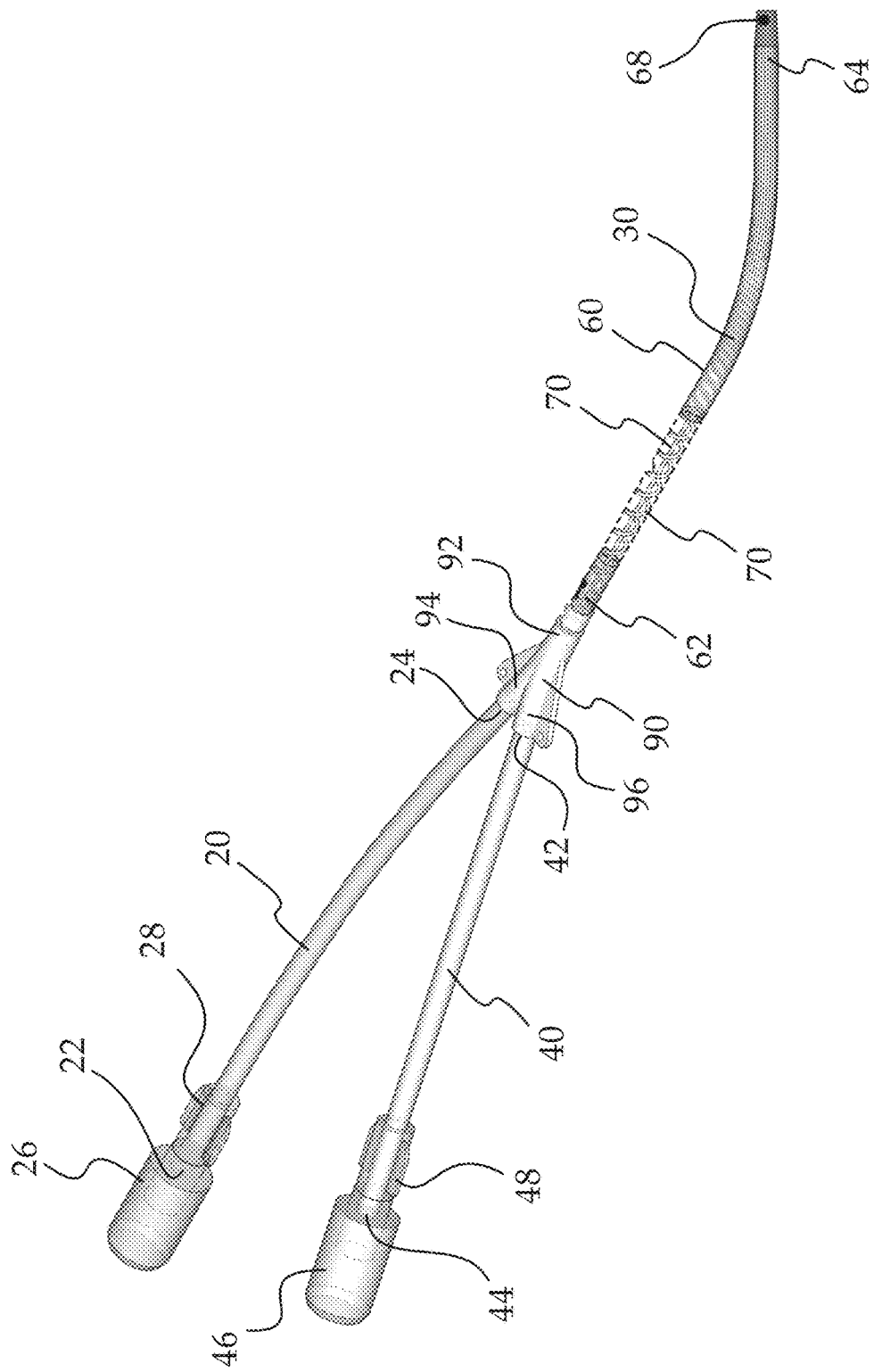
FIG. 2 is a perspective view of a dialysis tube coupled to an import tube and an export tube, according to the present disclosure.

FIG. 2 shows a perspective view of the dialysis tube 30 coupled with the import tube 20 and the export tube 40. The dialysis tube 30 includes an outer dialysis tube 60 and an inner dialysis tube 70, as will be described in greater detail below in reference to FIGS. 3 and 4. Referring to FIG. 2, the dialysis tube 30 has a first end 62 and a second, opposite end 64. The first end 62 is coupled to a "Y"-type lock 90. At the second end 64, the dialysis tube 30 includes a cap 68. The cap 68 may be in the form of a rigid head made of plastic, or any other suitable material for penetrating an artery and safely lasting within the artery for a predetermined period of time. The broken lines in FIG. 2 illustrate a cutaway view of the dialysis tube 30 to show the inner dialysis tube 70 for demonstration purposes only.

The "Y"-type lock 90 couples the outer dialysis tube 60 to the import tube 20 and the export tube 30. A first end 92 of the "Y"-type lock is wrapped around the dialysis tube 30. A second end 94 and a third end 96 of the "Y"-type lock 90, the ends of the fork or Y-shape of the "Y"-type lock 90, are wrapped around the import tube 20 and the export tube 40, respectively. It is to be understood that, while the "Y"-type lock 90 may be substantially Y-shaped, it can be made of any suitable size or shape to facilitate coupling the import tube 20 and the export tube 40 to the dialysis tube 30.

The import tube 20 has an inlet 22 and an outlet 24. The inlet 22 is coupled to a tube leading to the dialysate tank 10, the inlet 22 receiving fresh dialysate solution at a predetermined concentration of solutes. The outlet 24 is coupled to the second end 94 of the "Y"-type lock 90. Furthermore, the export tube 40 has an inlet 42 and an outlet 44. The inlet 42 is coupled to the third end 96 of the "Y"-type lock 90, the inlet 42 receiving used dialysate solution. The outlet 44 is coupled to another tube leading to the dialysate tank 10. The dialysate tank 10 may have separate compartments for fresh and used dialysate solution, or may have a single compartment in which the concentration of solutes is constantly monitored and adjusted accordingly.

Each of the import tube 20 and the export tube 40 includes a respective knob 26, 46 and lock 28, 48. The knobs 26, 46 facilitate separating the import tube 20 and the export tube 30. If complete separation is desired, rotating each knob 26, 46 will facilitate the import tube 20 and the export tube 40 separating from the inner dialysis tube 70 of the dialysis tube 30, and thereby disconnecting the import tube 20 and the export tube 40 from the dialysis tube 30.

Figure 4:
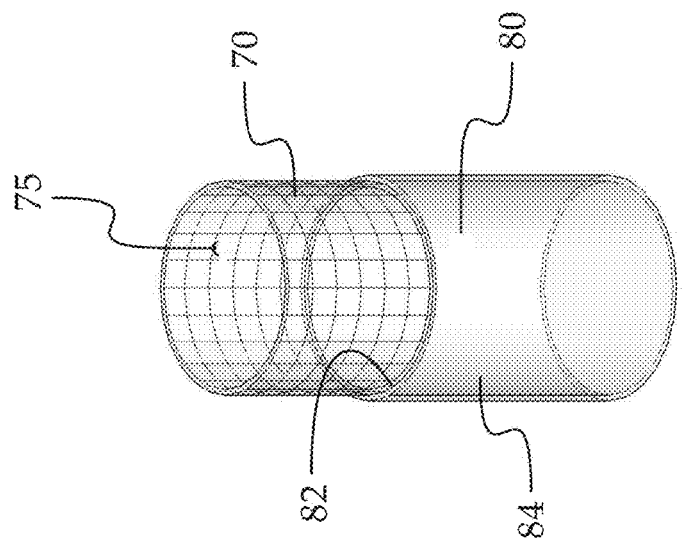
FIG. 4 is an enlarged cutaway view of the inner dialysis tube comprising a dialysis membrane, according to the present disclosure.
Figure 3:
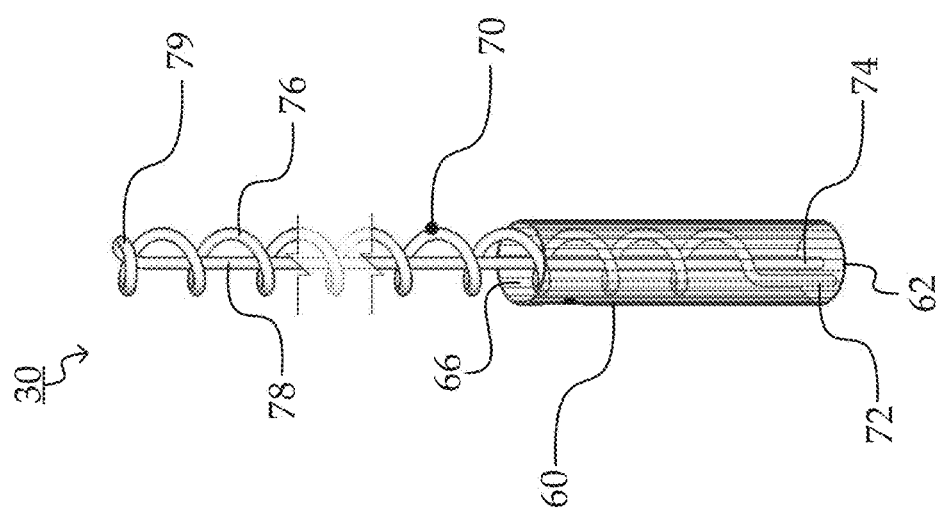
FIG. 3 is cutaway view of the dialysis tube having an outer dialysis tube and an inner dialysis tube, according to the present disclosure.

FIGS. 3-4 depict cutaway views of the dialysis tube 30. The dialysis tube 30 comprises an outer dialysis tube 60, an inner dialysis tube 70, and a dialysis membrane 80. As shown in FIG. 3, the inner dialysis tube 70 and the dialysis membrane 80 are disposed within an intermediate cavity 66 of the outer dialysis tube 60. An inlet 72 and an outlet 74 of the inner dialysis tube 70 are disposed at the first end 62 of the outer dialysis tube 60. The inlet 72 of the inner dialysis tube 70 is coupled to the outlet 24 of the import tube 20 and the outlet 74 of the inner dialysis tube 70 is coupled to the inlet 42 of the export tube 40. In certain embodiments, the "Y"-type lock 90 facilitates coupling the inlet 72 to the outlet 24 and the outlet 74 to the inlet 42.

The inner dialysis tube 70 has a first portion 76 and a second portion 78. In certain embodiments, the first portion 76 is a bending portion and the second portion 78 is a straight portion, in which the first portion 76 spirals around the second portion 78. The first portion 76 turns at an end 79 of the inner dialysis tube 70, which may be proximate to the second end 64 of the outer dialysis tube 60, to become the second portion 78. That is, in the present embodiment, dialysate solution flows in the inlet 72, through the first portion 76 towards the end 79, then through the second portion 78 and out of the outlet 74. In other embodiments, the first portion 76 and the second portion 78 form a double helix structure.

In either embodiment, bending or spiraling at least a portion of the inner dialysis tube 70 increases the surface contact area of the dialysis membrane 80 that coats the inner dialysis tube 70, which improves the efficiency of dialysis. Furthermore, in one or more embodiments, an exterior surface area 84 of the dialysis membrane 80 is completely exposed to and in contact with the intermediate cavity 66, further facilitating and improving the efficiency of dialysis. While FIG. 3 shows the inlet 72 disposed on the first portion 76 and the outlet 74 disposed on the second portion 78, in an alternative embodiment the inlet 72 and the outlet 74 may be switched such that dialysate solution enters through the inlet 72, through the second portion 78, past the end 79 into the first portion 76, and out of the outlet 74.

FIG. 4 illustrates that the inner dialysis tube 70 is generally cylindrical and is disposed within the dialysis membrane 80. A wall of the inner dialysis tube 70 is generally grid shaped and hollow, and supports the dialysis membrane 80. The inner dialysis tube 70 further includes an interior cavity 75. The interior cavity 75 disposed within the inner dialysis tube 70 is in partial fluid communication with the intermediate cavity 66 disposed within the outer dialysis tube 60. The intermediate cavity 66 of the outer dialysis tube 60, in turn, is in fluid communication with the artery of the patient.

During hemodialysis, dialysate solution flows within the interior cavity 75 and is exposed to an interior surface area 82 of the dialysis membrane 80. The exterior surface area 84 of the dialysis membrane 80 is exposed to the patient's blood, which is flowing through the intermediate cavity 66. By way of diffusion and ultrafiltration, excess water in the blood will flow through the dialysis membrane 80 to the dialysate solution. The dialysis membrane 80 is a semipermeable membrane having a plurality of pores, sized and shaped such that smaller solutes and fluid may pass through but larger molecules are blocked. As such, the interior cavity 75 is in partial fluid communication with the intermediate cavity 66 by way of the dialysis membrane 80.

Referring back to FIG. 3, the outer dialysis tube 60 has a wall which allows blood to flow from outside of the dialysis tube 30 and into contact with the dialysis membrane 80. In some embodiments, the outer dialysis tube is generally fence shaped and hollow. That is, the outer dialysis tube includes a plurality of longitudinal supports arranged in a generally cylindrical shape from the first end 62 to the second end 64. In one or more embodiments, the outer dialysis tube 60 is a protective hollow outer sleeve that effectively prevents damage to the inner dialysis tube 70 and dialysis membrane 80 before, during, and after implanting the dialysis tube 30 within an artery.

In some embodiments, the dialysis membrane 80 is made of a polyether sulfone, which facilitates biocompatibility and dialysis function. Due to the oxygen ether key in the molecular structure of the polyether sulfone material, the dialysis membrane 80 performs well in hydrophilic environments and is heat and corrosion resistant. When in contact with blood, the polyether sulfone will absorb less protein. In addition, when in contact with a strong oxidizer, the polyether sulfone will not produce free radicals and will lessen the activation of oxidation, and which better facilitates convection and diffusion.

Furthermore, in one or more embodiments, the inner dialysis tube 70 and the outer dialysis tube 60 are made of a medical silica gel, a polyurea amine ester, or other suitable material. In certain embodiments, a diameter of the inner dialysis tube 70 is between about 0.5 mm to 2.0 mm, while a length of the inner dialysis tube 70 is between about 200 mm and 300 mm. In certain embodiments, a diameter of the outer dialysis tube 60 is between about 3.0 mm to 5.0 mm, while a length of the outer dialysis tube 60 is between about 150 mm and 300 mm.

Operationally, the hemodialysis device 100 performs hemodialysis within an artery of a patient. By way of puncturing, the dialysis tube 30 is inserted into a femoral, or radial, artery in the human body though a thread or sheath pipe. In some embodiments, the cap 68 facilitates inserting the dialysis tube 30 into the artery. In certain embodiments, the dialysis tube 30 can be preserved in the artery for up to one week, although it is to be understood that the length of time the dialysis tube 30 can remain within the artery may vary depending on the status of the patient, materials used to construct the dialysis tube, etc.

The peristaltic pump 50 is then initiated to drive the dialysate solution through the hemodialysis device 100. The dialysate solution flows from the dialysate tank 10, through the import tube 20, into the inner dialysis tube 70. The dialysate solution in the inner dialysis tube 70 is of a high osmotic pressure, which extracts excess fluid out of the blood in the intermediate cavity 66 by the dialysis membrane 80. The dialysis membrane 80 has a permeability such that only molecules with less than a predetermined molecular weight may pass through, such as water. Excess fluid in the blood is thus sustainably penetrated into the dialysate solution, and then withdrawn from the body. It is to be understood that other wastes may also be removed from the blood by way of dialysis and ultrafiltration across the dialysis membrane.

Used dialysate solution and the excess fluid are withdrawn from the inner dialysis tube 70 through the outlet 74, and into the export tube 40. Meanwhile, dialysate solution of high concentration flows continuously through the inlet 72 of the inner dialysis tube 70 and maintains the high osmotic pressure to achieve dialysis. In some embodiments, a flow rate of the dialysate solution is adjusted by the speed regulating valve 55 and a temperature of the dialysate solution is adjusted by the temperature control device 15. When dialysis is stopped, the peristaltic pump 50 is shut down and the "Y"-type lock 90 and the locks 28, 48 are clipped, which allows the physician to temporarily stop the dialysate solution.

As such, hemodialysis is performed within the artery. As opposed to methods which require blood to be withdrawn from the body and pumped through a separate hemodialysis device, the hemodialysis device of the present disclosure will not, or at least minimally, affect the blood pressure of the patient. The patient is thus less at risk for complications.

In certain embodiments, the dialysis tube 30 is disposable and made of portable tubular parts for one-time use. Thus, hemodialysis may be performed on a patient bedside, performed efficiently for intensive treatment, and performed with reduced cost.

What is claimed is:

1. A hemodialysis device comprising:
an import tube having an inlet and an outlet;
an export tube having an inlet and an outlet;
a dialysis tube comprising:
  an outer dialysis tube having a first end, a second end, and an intermediate cavity;
  an inner dialysis tube disposed within the intermediate cavity, the inner dialysis tube having an inlet, an outlet, and an interior cavity, the inlet and the outlet disposed at the first end of the outer dialysis tube; and
  a dialysis membrane, the interior cavity being in partial fluid communication with the intermediate cavity across the dialysis membrane; and
a first lock coupling the outlet of the import tube to the inlet of the inner dialysis tube, and coupling the inlet of the export tube to the outlet of the inner dialysis tube.

2. The hemodialysis device recited in claim 1, further comprising:
a dialysate tank storing a dialysate solution, the dialysate tank coupled to the inlet of the import tube and the outlet of the export tube;
a pump that drives the dialysate solution through the import tube, the dialysis tube, and the export tube; and
a speed regulating valve.

3. The hemodialysis device recited in claim 2, further comprising a temperature control device that regulates a temperature of the dialysate solution.

4. The hemodialysis device recited in claim 1, wherein the import tube and the export tube each comprise a knob, the knobs facilitating decoupling the import tube and the export tube from the dialysis tube.

5. The hemodialysis device recited in claim 1, wherein the import tube and the export tube include a second lock and a third lock, respectively.

6. The hemodialysis device recited in claim 1, wherein the first lock is substantially Y-shaped and has a first end coupled to the first end of the outer dialysis tube, a second end coupled to the import tube, and a third end coupled to the export tube.

7. The hemodialysis device recited in claim 1, the inner dialysis tube comprising a first portion and a second portion, wherein the first portion spirals around the second portion.

* * * * *